United States Patent
Eshelman et al.

[11] Patent Number: 6,137,021
[45] Date of Patent: *Oct. 24, 2000

[54] CONVERSION OF AN HF ALKYLATION UNIT

[75] Inventors: Steven F. Eshelman, Elmhurst; Dennis E. O'Brien, Arlington Heights, both of Ill.

[73] Assignee: UOP LLC, Des Plaines, Ill.

[*] Notice: This patent is subject to a terminal disclaimer.

[21] Appl. No.: 09/372,116

[22] Filed: Aug. 20, 1999

Related U.S. Application Data

[62] Division of application No. 09/094,415, Jun. 9, 1998, Pat. No. 5,983,476.

[51] Int. Cl.$^7$ .................. C07C 15/067; C07C 2/64; C07C 2/68; C07C 2/56; C07C 2/58

[52] U.S. Cl. .................. 585/446; 585/464; 585/709; 585/723; 422/144; 422/146; 422/147; 422/187; 422/188; 422/189; 422/198

[58] Field of Search .................. 585/446, 464, 585/704, 723; 422/144, 146, 147, 187, 188, 189, 198

[56] References Cited

U.S. PATENT DOCUMENTS

| | | | |
|---|---|---|---|
| 3,342,886 | 9/1967 | Pasky | 585/464 |
| 3,906,054 | 9/1975 | Kaeding et al. | 585/722 |
| 3,956,416 | 5/1976 | Vora | 260/683.48 |
| 4,024,200 | 5/1977 | Vora | 585/464 |
| 4,046,516 | 9/1977 | Burton et al. | 585/464 |
| 4,503,277 | 3/1985 | Himes | 585/464 |
| 4,891,466 | 1/1990 | Kocal | 585/464 |
| 5,157,158 | 10/1992 | Berna Tejero et al. | 585/628 |
| 5,196,574 | 3/1993 | Kocal | 562/94 |
| 5,302,732 | 4/1994 | Steigleder et al. | 554/98 |
| 5,344,997 | 9/1994 | Kocal | 568/628 |
| 5,491,271 | 2/1996 | Marinangeli et al. | 585/446 |
| 5,663,474 | 9/1997 | Pham et al. | 585/446 |
| 5,856,606 | 1/1999 | Oroskar | 585/446 |

OTHER PUBLICATIONS

*Handbook of Petroleum Refining Processes* Edited by: Robert A. Meyers (New York, McGraw–Hill, 2$^{nd}$ Edition 1997) pp. 1.53–1.66 ISBN 0–07–041796–2 TP690.H34.

Primary Examiner—Marian C. Knode
Assistant Examiner—Thuan D. Dang
Attorney, Agent, or Firm—John G. Tolomei; John F. Spears, Jr.; Michael A. Moore

[57] ABSTRACT

A method of converting an HF alkylation process into a solid catalyst alkylation process is disclosed. In this method, an HF alkylation unit having an HF stripper downstream of the HF alkylation reactor is modified to a benzene rectifier. By modifying the HF stripper, this invention not only makes use of the existing HF stripper but also allows the entire downstream product recovery section, which comprises four fractionation columns, to be used in the modified process with only relatively minor modifications. Thus this invention maximizes the use of existing equipment and minimizes the investment necessary to eliminate the use of HF in detergent alkylation.

7 Claims, 2 Drawing Sheets

6,137,021

CONVERSION OF AN HF ALKYLATION UNIT

CROSS-REFERENCE TO RELATED APPLICATION

This application is a divisional application of U.S. patent application Ser. No. 09/094,415, filed Jun. 9, 1998 now U.S. Pat. No. 5,983,476.

FIELD OF THE INVENTION

The invention relates to the alkylation of aromatic compounds with olefins using hydrogen fluoride (HF) and solid catalyst. More specifically, this invention relates to the apparatus for performing HF and solid catalyst alkylation.

BACKGROUND OF THE INVENTION

About thirty years ago it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured world-wide.

LABS are manufactured from linear alkylbenzenes (LAB). The petrochemical industry produces LAB by dehydrogenating linear paraffins to linear olefins and then alkylating benzene with the linear olefins in the presence of HF. This is the industry's standard process. Over the last decade, environmental concerns over HF have increased, leading to a search for substitute processes employing catalysts other than HF that are equivalent or superior to the standard process. Solid alkylation catalysts, for example, are the subject of vigorous, ongoing research.

To date, alkylation processes that use catalysts other than HF, that is, commercially available solid alkylation catalysts, tend to operate at a higher molar ratio of benzene per olefin than processes that employ HF. As an illustration, while detergent alkylation processes that use HF tend to operate at a benzene/olefin molar ratio of 12:1 to 6:1, alkylation processes that use commercially available solid alkylation catalysts tend to run at higher benzene/olefin ratios, typically 30:1 to 20:1. One reason for this is that solid alkylation catalysts tend to be less selective toward producing monoalkylbenzene, and therefore the benzene/olefin molar ratio must be increased to meet increasingly stringent selectivity requirements. Selectivity, which is often defined as the weight ratio of monoalkylbenzene product to all products, is expected in some areas to be 85–90% near term, increasing to 90–95% by about the year 2000. Incidentally, a higher benzene/olefin ratio not only tends to increase selectivity but also often produces other benefits for solid alkylation catalysts, including improving olefin conversion, monoalkylbenzene linearity, and catalyst life.

One configuration of an HF detergent alkylation unit that gained wide acceptance during the 1970's and 1980's uses an HF alkylation reaction section, an HF regeneration section, and an HF sludge treatment section. It is not necessary here to describe these three sections in detail, but one of the compelling reasons for switching from HF to a solid catalyst is that building and operating these three HF-containing sections have often proven to be troublesome, complex, and expensive. In addition to these three sections, this HF detergent alkylation unit also uses a series of five product recovery columns to produce a monoalkylbenzene product stream from the alkylation reaction effluent, which contains not only monoalkylbenzene but generally also benzene, paraffins, by-products, and HF. The first of the five product recovery columns is usually called an HF stripper, which strips HF from the alkylation reaction effluent for recycle to the HF alkylation reactor. The second column is generally called a benzene column, which is a distillation column that removes benzene from the HF stripper bottom stream as an overhead stream which is recycled to the HF alkylation reactor. Then, the remaining hydrocarbons flow to a series of three distillation columns: a paraffin column which removes the paraffins as a sidecut for recycle to a paraffin dehydrogenation unit if present, an LAB rerun column which removes LAB from the paraffin column bottom stream and produces an overhead stream containing the LAB product, and a heavy alkylate rerun column that removes heavy alkylate by-products including polyalkylbenzenes.

Changing from HF to a solid catalyst has greatly diminished the utility of this five-column product recovery train in existing HF detergent alkylation units, particularly in two aspects. First, the change to a solid catalyst eliminates the need for HF stripping, thereby rendering the existing HF stripper redundant. Second, the higher benzene/olefin molar ratio (e.g., 20:1 as opposed to 8:1) in the alkylation reactor more than doubles the flow of benzene to the existing benzene column, thereby flooding the existing benzene column. Too small for the higher recycle benzene flow, the existing benzene column must be replaced or supplemented with an entirely new benzene column, which greatly increases the capital cost of converting from HF to solid catalyst. But, even if a new benzene column was not needed, the operating costs of the now-converted solid catalyst unit would be much higher, because of the additional cost of the energy required to distill and condense the larger quantity of excess benzene from the alkylation reaction effluent.

Accordingly, a method is sought that reduces the cost of converting an existing detergent alkylation unit from HF to a solid alkylation catalyst. A process that can reduce the cost of recycling benzene and thereby improve the usefulness of commercially available solid alkylation catalyst will help avoid the need for using HF in detergent alkylation processes.

SUMMARY OF THE INVENTION

This invention is a method of converting an existing detergent alkylation process from HF to a solid catalyst that maximizes the use of existing equipment and minimizes the cost of recycling excess benzene to the alkylation reactor. In the form that is believed to become the most popular of all possible conversion options, the conversion method calls for the modification of the HF stripper in an HF alkylation process for use as a benzene rectifier in a solid catalyst alkylation process. In a broad embodiment, this invention is method of converting an HF alkylation unit into a solid catalyst alkylation unit. The method comprises providing an HF alkylation reactor that produces a reactor effluent comprising alkyl aromatics and in which the alkylation takes place in the presence of HF. In addition, a stripping vessel for removing HF from the reactor effluent is provided. The stripping vessel has an upper inlet port, which is in communication both with the HF alkylation reactor and with an upper portion of the stripping vessel. The function of the upper inlet port is to transfer hydrocarbons from the HF alkylation reactor to the upper portion of the stripping vessel. The stripping vessel also has an HF outlet port, which is in communication both with the upper portion of the stripping vessel and with the HF alkylation reactor. The function of the HF outlet port is to transfer HF from the upper portion of the stripping vessel to the HF alkylation reactor. Also provided is a distillation vessel, which is in communication with a lower portion of the stripping vessel and which functions to recover the alkyl aromatics. The method further comprises replacing the HF alkylation reactor with a solid catalyst alkylation reactor for producing the alkylation effluent in the presence of a solid alkylation catalyst. The method further comprises modifying the stripping vessel to function as a rectifying vessel by adding a lower inlet port and replacing the HF outlet port with a hydrocarbon outlet port. The lower inlet port is in communication with the solid catalyst alkylation reactor and with a lower portion of the stripping vessel and functions to transfer hydrocarbons from the solid catalyst alkylation reactor to the lower portion of the stripping vessel. The hydrocarbon outlet port is in communication with an upper portion of the stripping vessel and with the solid catalyst alkylation reactor, and functions to transfer hydrocarbons from the upper portion of the stripping vessel to the solid catalyst alkylation reactor.

Other embodiments and aspects of the present invention encompass further details related to the replacement and addition of equipment to effect modification of the unit and the operation of the unit modified in accordance with this invention.

INFORMATION DISCLOSURE

LAB processes are described in the book edited by Robert A. Meyers entitled *Handbook of Petroleum Refining Processes,* (McGraw-Hill, New York, Second Edition, 1997) at pages 1.53 to 1.66, the teachings of which are incorporated herein by reference.

Solid catalysts comprising fluorided silica-alumina for alkylating aromatics are disclosed in U.S. Pat. Nos. 5,196,574 (Kocal), 5,344,997 (Kocal), and 5,302,732 (Steigleder et al.). The teachings of the '574, '997, and '732 patents are incorporated herein by reference.

DETAILED DESCRIPTION OF THE INVENTION

The present invention in its method aspects consists of steps for changing the function of an existing HF detergent alkylation unit. HF alkylation units to which this method can be applied will have an HF alkylation reactor, an HF stripping vessel commonly called an HF stripper which is in communication with the alkylation reactor, and a distillation column generally called a benzene column which is in communication with the HF stripper. It is anticipated that this method of conversion will accompany the replacement of the HF alkylation reactor with a reactor more specifically suited for alkylation in the presence of a solid alkylation catalyst. Of course, it is also possible that the existing HF alkylation reactor might not be replaced but might instead be modified to function as a solid catalyst alkylation reactor. However, it is believed that the operating conditions of a solid catalyst alkylation reactor are sufficiently different from those of an HF alkylation reactor that it is more practical and economical for the operation of the solid catalyst alkylation process to replace rather than to modify the HF alkylation reactor. Irrespective of whether the HF alkylation reactor is replaced or modified, the use of this invention will usually be accompanied by a decrease in HF usage and in the environmental concerns over the use of HF.

Figure 1:
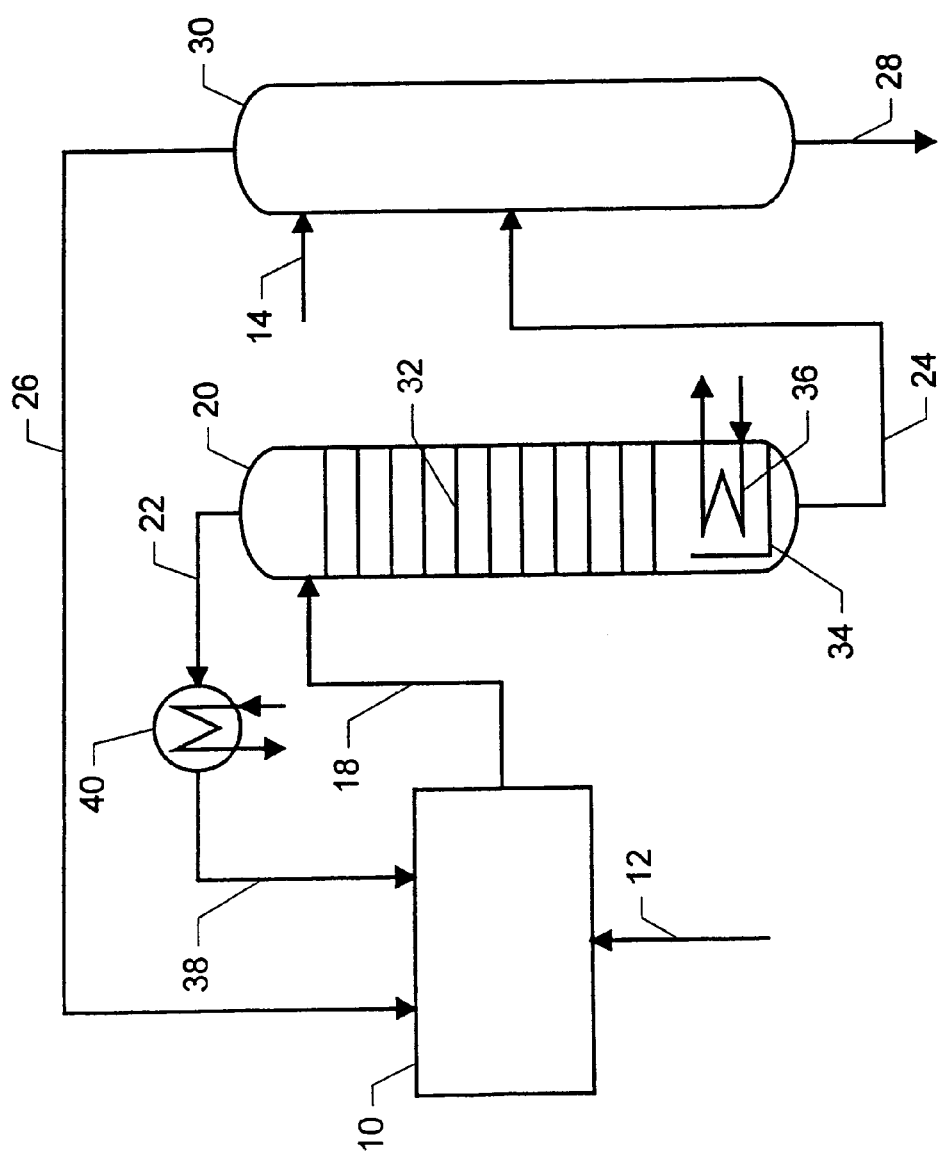
FIG. 1 is a process flow diagram of a HF detergent alkylation process before conversion.

Reference is now made to FIG. 1 in order to show the type of HF alkylation unit to which the method of this invention may be applied. Looking now at FIG. 1, a traditional HF detergent alkylation unit will have an HF alkylation reactor 10, an HF stripper 20, and a benzene column 30. An olefin-containing stream, which typically contains paraffins also, enters HF alkylation reactor 10 through a line 12. Recycle benzene enters the HF alkylation reactor 10 through a line 26. HF alkylation reactor 10 typically comprises an acid storage drum, one or more acid mixers, one or more acid settlers, pumps, exchangers, and lines that are not shown in FIG. 1 but are known to a person of ordinary skill in the art of HF alkylation. The effluent of the HF alkylation reactor 10 typically contains LAB, unreacted benzene, unreacted paraffins, by-products including polyalkylbenzenes and oligomers, as well as HF. The alkylation reactor effluent flows through a line 18 and enters the HF stripper 20. HF stripper 20 employs sieve trays, which are schematically shown and one of which is denoted as 32 in FIG. 1, and the feed point is above the uppermost sieve tray. The HF stripper 20 removes HF from the alkylation reactor effluent, and the stripped HF vapors pass through a line 22, are condensed in a condenser 40, and recycle to the HF alkylation reactor 10 through a line 38. An internal bayonet-tube reboiler 36 situated in a space defined in part by a baffle 34 and below the lowermost sieve tray within the HF stripper 20 provides heat for HF stripping. The HF stripper bottoms stream flows through a line 24 to a benzene column 30. Make-up benzene, which generally has been dried to remove water, enters the process via a line 14 to the benzene column 30. Benzene column 30 removes excess benzene from the HF stripper bottoms and recycles benzene to the HF alkylation reactor 10 through the line 26. The benzene column bottoms stream flows through a line 28 to conventional product recovery facilities, which are not shown in FIG. 1.

The alkylation reactor effluent in the line 18 usually will have volumetric ratio of HF per hydrocarbon content of generally from about 1.0:1 to about 1.5:1, a molar ratio of benzene per LAB of generally from about 5:1 to about 30:1 and more commonly from about 5:1 to about 12:1, and a temperature of generally from about 176 to about 284° F. (80 to 140° C.). The HF stripper has generally about 10 to 20 separation stages and usually uses sieve trays with a tray efficiency of about 60%. Thus, the HF stripper generally has from about 15 to about 25 trays, and typically 20 trays. The alkylation reactor effluent usually enters totally in the liquid phase stream above the uppermost separation stage or tray. Located below the lowermost separation stage or tray, the reboiler for the HF stripper normally comprises bayonet-style heat exchanger tubes inserted into the HF stripper, but the reboiler may also be external to the HF stripper, with conduits carrying fluids back and forth between the reboiler and the HF stripper. A heating fluid, typically hot oil or steam, circulates through the bayonet tubes and is collected from the tubes. Contact of the hydrocarbons with the tubes may be either in flow-through mode or in backmix mode. The HF stripper typically uses no overhead condenser and hence has no reflux is returned to the stripper, although the net overhead vapor is typically condensed and recycled to the HF alkylation reactor as a liquid. The operating conditions of the HF stripper include a pressure of from about 50 to about 70 psi(g) (345 to 483 kPa(g)), a bottoms temperature of from about 250° to about 300° F. (121° to 149° C.), an overhead temperature of from about 100° to about 150° F. (38° to 66° C.), which are sufficient to remove substantially all of the HF from the entering HF reaction effluent stream. Under these conditions, the bottoms product of the HF stripper typically contains less than 100 wppm HF, and preferably less than 10 wppm HF, and generally has a molar ratio of benzene per LAB of approximately 5:1 to 9:1. The overhead vapor stream of the HF stripper typically contains a mixture of HF and benzene, with a benzene concentration of about 50 wt-% and an HF concentration of about 50 wt-%, but these concentrations can vary over wide ranges. Operating at these conditions, the vessel shell of the HF stripper typically comprises unlined killed carbon steel. Internal equipment within the HF stripper, such as trays, baffles, and the reboiler, have a similar metallurgy.

The HF stripper bottoms stream passes to a benzene column, which removes the remainder of the benzene using typically from 45 to 55 sieve trays, usually about 50 sieve trays. The HF stripper bottoms stream enters at or around sieve tray 30, as numbered from the top of the benzene column. Makeup benzene, which has been previously dried, is also fed to the benzene column, typically at a location above the uppermost tray of the benzene column. Both the makeup benzene and the HF stripper bottoms streams are generally in the liquid phase. The benzene column usually employs a reboiler as well as a total condenser for the overhead stream, which refluxes liquid to the top of the benzene column. As used herein the term "total condenser" means a heat exchanger which condenses a vapor or mixture of vapors, condensing generally more than 95 wt-%, and more commonly more than 99.5 wt-% of the vapors. The operating conditions of the benzene column include a pressure of about 10 psi(g) (69 kPa(g)), an overhead temperature of about 200° F. (93° C.), and a bottom temperature of about 450° F. (232° C.). The benzene column produces a net overhead liquid stream which contains benzene and may also contain a small concentration (typically less than 100 wppm) of paraffins, and a bottom stream containing linear alkylated benzenes and paraffins and which may also contain a low concentration (typically less than 100 wppm) of benzene.

In accord with this invention, the HF stripper vessel along with its internals, as usually encountered, is suitable for modifying to a benzene rectifier for use in separating the effluent of a solid catalyst alkylation reactor. It is well known in the art that a rectifier and a stripper are distinctly different both in their appearance and function. The differences between a rectifier and a stripper are readily apparent by considering distillation processes in general. Distillation processes rely on the well-known tendency that when liquid and vapor phases contact, the more volatile components tend to concentrate more in the vapor phase than in the liquid phase. In single-stage operation, this concentration of the more volatile component in the vapor phase is achieved by partially vaporizing a liquid mixture and then separating the liquid and vapor phases. In multi-stage operation, a liquid descends a vertical distillation column and passes through a number of stages in which it is contacted counter currently by ascending vapor. The point at which feed is introduced to the distillation column divides the column into two sections. The stripping section is below the feed point, and the rectifying section is above the feed point. In the stripping section, the more volatile component is stripped from the descending liquid. In the rectifying section, the concentration of the less volatile component in the vapor is reduced.

In practice, the stages in which the streams of liquid and vapor contact each other may be trays or packing material.

Therefore, a stripper is different in one aspect from a rectifier in that the feed to a stripper is at the top of a number of stages, whereas the feed to a rectifier is at the bottom of a number of stages. In another aspect, a stripper is different from a rectifier in that a stripper strips the more volatile component from the descending liquid, whereas a rectifier reduces the concentration of the less volatile component in the vapor. Thus, a stripper does not function as a rectifier, and where the art teaches the use of a rectifier, a person of ordinary skill in the art would not replace the rectifier with a stripper. Accordingly, a person of ordinary skill views a stripper and a rectifier as two distinct methods of separation.

As previously mentioned, this invention comprises modifying the HF stripper to function as a benzene rectifier. Without this modification, the stripper is not suitable for use in a solid catalyst alkylation process. Solid catalyst alkylation processes tend to produce an alkylation reactor effluent that contains far less HF and much more benzene than the alkylation reactor effluent that is produced by HF alkylation reactors. The reactor effluent from a solid catalyst alkylation processes contains generally less than 1 wppm HF, and usually less than 0.01 wppm HF, and a molar ratio of benzene per LAB of from about 20:1 to about 30:1. If the effluent of a solid catalyst alkylation reactor was passed to the top of an unmodified stripper, with no separation stages or trays between the feed point and the overhead stream withdrawal point, the stripper overhead stream would contain not only benzene but also a substantial amount of LAB. Thus, recycling of the stripper overhead stream would recycle LAB to the alkylation reactor. But recycling LAB decreases olefin utilization because valuable olefins alkylate LAB instead of benzene. In addition, recycling LAB decreases LAB yield because alkylating LAB produces heavy alkylate product. Thus, without modification, the HF stripper is unsuitable for use in solid catalyst alkylation process. On the other hand, when the alkylation reactor effluent is introduced to the bottom of a benzene rectifier, one or more separation stages or fractionation trays are interposed between the feed point and the overhead stream withdrawal point. These stages or trays decrease the LAB content of the rectifier overhead stream, which improves olefin utilization and LAB yield.

This invention of modifying the HF stripper to a benzene rectifier is applicable to conversions from HF alkylation processes to other alkylation processes which produce alkylation reactor effluents similar to those in solid catalyst alkylation processes and which must separate alkylation reactor effluents to a degree that is similar to that in solid catalyst alkylation processes. It is believed that this invention will be most applicable to conversions to solid catalyst alkylation processes, and therefore most of the discussion that follows is directed to conversions to solid catalyst alkylation processes. However, this invention is not limited to such conversions and conversions to other alkylation processes that use other alkylation catalysts may also be suitable for use with this invention.

Figure 2:
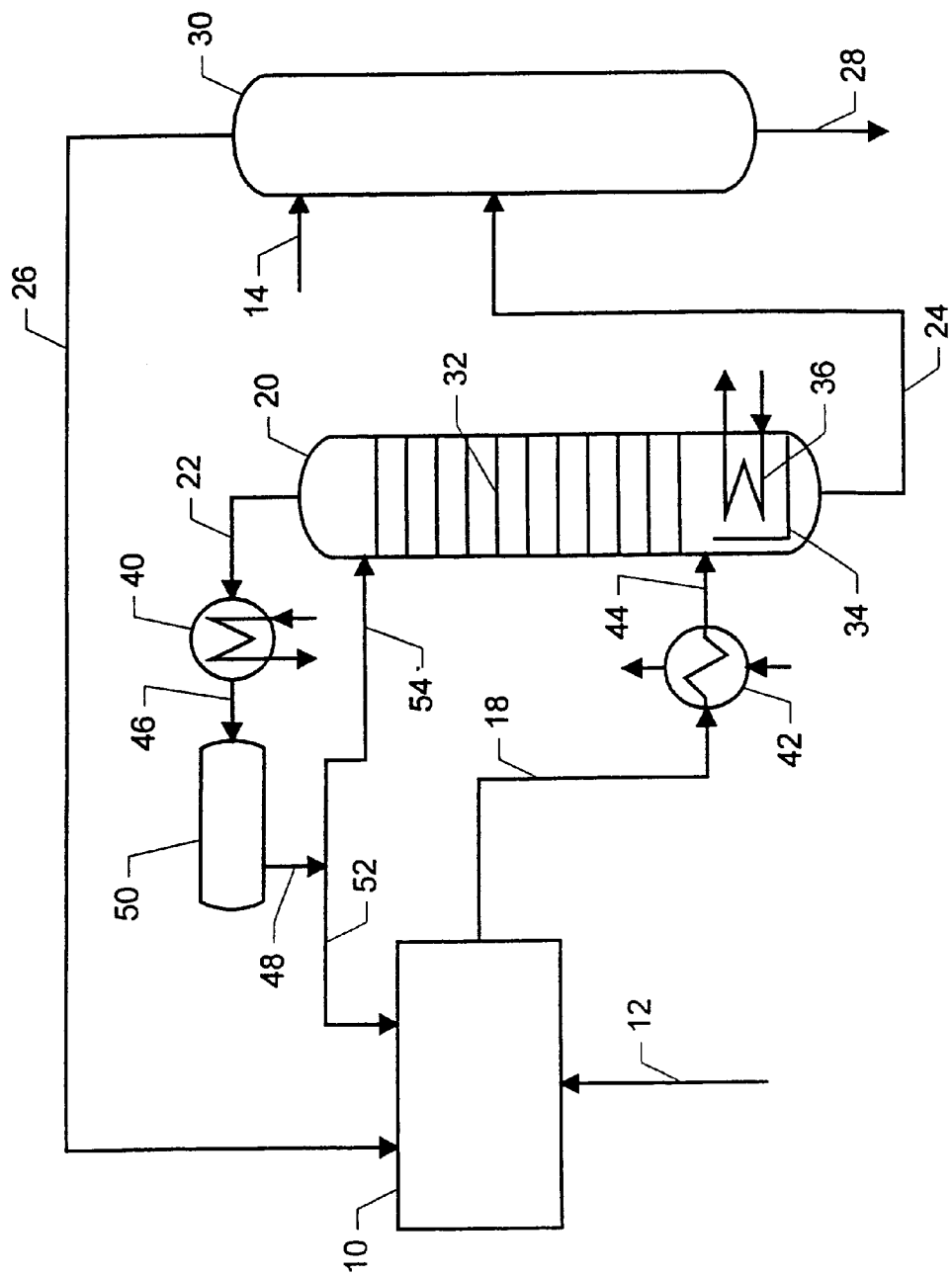
FIG. 2 is a process flow diagram of a solid catalyst detergent alkylation process, including an HF stripper that has been modified in accord with this invention.

In accord with the present invention in which the HF detergent alkylation unit is modified to become a solid alkylation catalyst detergent alkylation unit, the HF stripper is modified to become the benzene rectifier. Referring now to FIG. 2, FIG. 2 shows the HF alkylation unit of FIG. 1 after conversion into a solid catalyst alkylation unit, and equipment in FIG. 2 that corresponds to equipment in FIG. 1 has the same item number in both Figures. To avoid repetition, items already described in FIG. 1 are not described again in FIG. 2. An olefin-containing stream, which also usually contains paraffins, flows through a line 12 to the solid catalyst alkylation reactor 10. Recycle benzene enters the solid catalyst alkylation reactor 10 through lines 26 and 52. Solid catalyst alkylation reactor 10 typically comprises one or more solid catalyst fixed or moving beds, pumps, exchangers, and lines and valves so that at any given time one or more of the beds can be in service or out of service for catalyst rejuvenation or regeneration. Typically there are at two solid catalyst beds, with one bed on-line and the other off-line at any given time. Such equipment is known to a person of ordinary skill in the art of hydrocarbon processing and is therefore not shown in FIG. 2 or described herein. The effluent of solid catalyst reactor 10 flows through a line 18. Because the solid catalyst alkylation reactor 10 normally operates at a liquid phase, the alkylation reactor effluent is normally in the liquid phase. However, it may be preferred to use some preheating to heat or partially vaporize the effluent prior to entering benzene rectifier 20. Accordingly, the alkylation reactor effluent in the line 18 is heated further in an indirect heat exchanger 42 using any suitable heating medium, such as hot oil. Then the alkylation reactor effluent flows through a line 44 into benzene rectifier 20. The entering heated reactor effluent stream enters below the bottom of the lowermost of the sieve trays, one of which is denoted as 32 in FIG. 2.

The benzene rectifier typically employs the same metallurgy for the rectifier shell as well as for the internals of the HF stripper. In addition, the benzene rectifier employs the same number and type of separation stages or trays as the HF stripper, although fewer trays could also be used and some or all of the trays could be replaced with a vapor-liquid contacting media, such as regular-shaped Berl saddles or Raschig rings in a random arrangement or such as structured elements in an ordered arrangement. The benzene rectifier can employ the reboiler that was present in the HF stripper, however additional reboiling heat is usually required and this additional heat may be provided by adding an external reboiler or, as shown in FIG. 2, by a feed preheater for the feed to the benzene rectifier. Whereas the HF stripper used no overhead condenser, the benzene rectifier employs a total condenser, and the HF stripper must be modified accordingly. A portion of the condensed overhead stream is refluxed to the upper portion of the benzene rectifier, usually to a location above the uppermost tray of the benzene rectifier. Thus, the overhead stream of the benzene rectifier 20 passes through a line 22 to a total condenser 40, and the condensed overhead stream flows through a line 46 to an overhead receiver 50. The liquid phase from receiver 50 flows through a line 48, and one portion returns to the benzene rectifier as reflux through a line 54 and another portion recycles to the alkylation reactor 10 through a line 52.

The operating conditions of the benzene rectifier include a pressure of from about 50 to about 70 psi(g) (345 to 483 kPa(g)), although higher pressures up to the design limit of the vessel may be employed. Thus, the design pressure of the HF stripper may set the upper limit on operating pressure when the HF stripper is modified into a benzene rectifier. The overhead temperature of the benzene rectifier is normally about 300° F. (149° C.) and the bottom temperature is generally also about 300° F. (149° C.). Thus, the benzene rectifier operates with a relatively small difference between the overhead and bottom temperatures, which is a consequence of the abundance of benzene in the benzene rectifier. Despite driving a substantial amount of benzene from the alkylation reactor effluent into the benzene rectifier overhead stream, the benzene rectifier generally produces a bottom stream that nevertheless contains a sufficient amount of benzene such that the boiling point of the bottom stream is relatively close to that of the overhead stream. Of the total amount of benzene entering the benzene rectifier with the alkylation reactor effluent, generally about 50 percent to about 70 percent exits with the net overhead stream and the remainder exits with the net bottoms stream.

The net bottom stream of the benzene rectifier passes to the benzene column. One of the advantages of this invention is that the same benzene column that was employed in the HF alkylation process before modification can also be employed as the benzene column in the alkylation process after modification in accord with this invention. Thus, this invention maximizes the use of existing equipment. The same benzene column can be used even when the alkylation process after modification employs a solid alkylation catalyst, despite the fact that the alkylation reactor effluent contains three or four times as much benzene as the HF alkylation effluent. This capability of employing the existing vessel from the HF process in the solid catalyst process is directly attributable to this invention's modification of the existing vessel for the HF stripper in the HF process as a benzene rectifier in the solid catalyst alkylation process. The benzene rectifier produces a benzene rectifier bottom stream that has a sufficiently low molar ratio of benzene per LAB (e.g., typically 7:1) such that the bottom stream can be fed directly to the benzene column that had been used in the HF process.

When downstream of the benzene rectifier, the benzene column has a generally similar arrangement and operates at generally similar conditions as those used when the benzene column was downstream of the HF stripper. Accordingly, the benzene column uses approximately 50 sieve trays, the benzene rectifier bottom stream enters at approximately sieve tray 30, as numbered from the top of the column, makeup benzene to the process is introduced to the benzene column (but pre-drying of the makeup benzene is not needed), an overhead total condenser is used, a portion of the condensed liquid overhead stream is refluxed to the benzene column, the pressure is of about 10 psi(g) (69 kPa(g)), the overhead temperature is about 200° F. (93° C.), the bottom temperature is about 450° F. (232° C.). A net overhead liquid stream from the benzene column recycles to the alkylation reactor.

In an alkylation process that has been modified in accord with this invention, the benzene column bottoms stream passes to the same product recovery section to which the benzene column bottoms stream passes in the alkylation process before modification. This is another advantage of this invention, which maximizes the use of existing equipment while modifying the alkylation process. This product recovery section, which is conventional and need not be described in detail herein, generally includes a paraffin column, an LAB rerun column, and a heavy alkylate rerun column.

The description of this invention in the context of this specific embodiment is not meant to limit the scope of this invention to the embodiment shown herein. In particular, the suggested reuse of various existing items of equipment such as reboilers, trays, inlet distributors, and lines are not intended to limit the scope of this invention to a conversion that makes use of specific items apart from the HF stripper.

What is claimed is:

1. A method of converting an HF alkylation unit into a solid catalyst alkylation unit, comprising providing (1) an HF alkylation reactor for producing in the presence of HF a reactor effluent comprising alkyl aromatics, (2) a stripping vessel for removing HF from the reactor effluent, the stripping vessel having an upper inlet port in communication with the HF alkylation reactor and with an upper portion of the stripping vessel for transferring hydrocarbons from the HF alkylation reactor to the upper portion of the stripping vessel and an HF outlet port in communication with the upper portion of the stripping vessel and with the HF alkylation reactor for transferring HF from the upper portion of the stripping vessel to the HF alkylation reactor, (3) a distillation vessel in communication with a lower portion of the stripping vessel for recovering the alkyl aromatics, the method further comprising modifying the HF alkylation reactor to function as a solid catalyst alkylation reactor for producing the alkylation effluent in the presence of a solid alkylation catalyst, and the method further comprising modifying the stripping vessel to function as a rectifying vessel by:

a) adding a lower inlet port in communication with the HF alkylation reactor and with a lower portion of the stripping vessel for transferring hydrocarbons from the HF alkylation reactor to the lower portion of the stripping vessel, and b) replacing the HF outlet port with a hydrocarbon outlet port in communication with an upper portion of the stripping vessel and with the HF alkylation reactor for transferring hydrocarbons from the upper portion of the stripping vessel to the solid catalyst alkylation reactor.

2. The method of claim 1 wherein the step of modifying of the stripping vessel comprises installing a heat exchanger in the unit for withdrawing heat from an upper portion of the stripping vessel.

3. The method of claim 2 wherein the step of modifying of the stripping vessel comprises adding a heat exchanger inlet conduit in communication with the upper portion of the stripping vessel and with the heat exchanger for transferring hydrocarbons from the stripping vessel to the heat exchanger and adding a heat exchanger outlet conduit in communication with the heat exchanger and with the upper portion of the stripping vessel for transferring hydrocarbons from the heat exchanger to the stripping vessel.

4. The method of claim 3 wherein the heat exchanger inlet conduit is in communication with the hydrocarbon outlet port.

5. The method of claim 3 wherein the heat exchanger outlet conduit is in communication with the upper inlet port.

6. The method of claim 1 wherein the stripping vessel is vertically oriented and contains at least one separation stage and the upper portion of the stripping vessel is above the uppermost separation stage.

7. The method of claim 1 wherein the stripping vessel is vertically oriented and contains at least one separation stage and the lower portion of the stripping vessel is below the lowermost separation stage.

* * * * *